(12) United States Patent
Howard et al.

(10) Patent No.: US 6,228,487 B1
(45) Date of Patent: May 8, 2001

(54) POLY(VINYL ACETAMIDE) ADHESIVE FOR SKIN CLEANING TAPE

(75) Inventors: Doreen L. Howard, Plainsboro; Gary T. Martino, Jamesburg; Ian W. Cottrell, Princeton, all of NJ (US)

(73) Assignee: National Starch and Chemical Investment Holding Corporation, Wilmington, DE (US)

(*) Notice: Subject to any disclaimer, the term of this patent is extended or adjusted under 35 U.S.C. 154(b) by 0 days.

(21) Appl. No.: 09/224,542

(22) Filed: Dec. 31, 1998

(51) Int. Cl.[7] .................. C09J 7/02; A61K 7/48
(52) U.S. Cl. .............. 428/355 CN; 428/474.4; 424/401; 424/78.03; 514/859
(58) Field of Search ............... 428/355 CN, 474.4; 424/78.03, 401; 514/859

(56) References Cited

U.S. PATENT DOCUMENTS

| 4,018,826 | 4/1977 | Gless, Jr. et al. ............... 260/583 P |
| 4,126,142 | * 11/1978 | Saute ........................................ 132/7 |
| 4,774,022 | * 9/1988 | Sumi et al. ........................... 252/500 |
| 4,942,259 | 7/1990 | Parris et al. ......................... 564/187 |
| 5,026,552 | * 6/1991 | Gueret et al. ........................ 424/401 |
| 5,512,277 | * 4/1996 | Uemura et al. .................... 424/78.03 |
| 5,968,537 | * 10/1999 | Crotty et al. ........................ 424/402 |

FOREIGN PATENT DOCUMENTS

| 8-81428 | 3/1996 | (JP) .............................. C07C/233/05 |
| 8-134029 | 5/1996 | (JP) .............................. C07C/233/05 |
| WO 97/32567 | 9/1997 | (WO) .............................. A61K/7/48 |
| WO 98/05283 | 2/1998 | (WO) .............................. A61F/13/12 |
| WO 98/42302 | 10/1998 | (WO) .............................. A61K/7/00 |
| WO 98/42304 | 10/1998 | (WO) .............................. A61K/7/48 |

* cited by examiner

Primary Examiner—Daniel Zirker
(74) Attorney, Agent, or Firm—Thomas F. Roland

(57) ABSTRACT

This invention involves skin cleaning products and tapes for removing keratotic plugs, dirt and other debris found on the skin and in skin pores and comprising a poly(vinyl acetamide) polymer based adhesive composition applied to a substrate backing material.

20 Claims, No Drawings

POLY(VINYL ACETAMIDE) ADHESIVE FOR SKIN CLEANING TAPE

BACKGROUND OF THE INVENTION

This invention relates to the use of selected poly(vinyl acetamide) based adhesives in skin cleaning tapes to remove keratotic plugs as well as dirt and other matter from skin and skin pores.

Keratotic plugs are dead epidermal cells and oil which together with sebum, dirt and other skin debris can block and plug the pores of the skin. The formation of such plugs and skin build up are often conspicuous and can provide undesirable cosmetic effects. Additionally, if proper treatment is not given and these plugs and other build ups are not removed, various skin problems can arise.

Since keratotic plugs are formed deep in the skin, the use of traditional cleansers and detergents like soap, make-up removers and face masks are usually not effective in their removal. There have been some recent disclosures of skin cleaning compositions or methods to alleviate this problem. One method shown to remove keratotic plugs is found in U.S. Pat. No. 5,512,277 issued on Apr. 30, 1996 to T. Uemura et al., which discloses the use of synthetic cationic polymer compositions containing salt forming groups. In WO/32567 published on Sep. 12, 1997, a peel off type sheet pack is disclosed that comprises a multi-layer moisture-permeable support that includes a keratotic plug removing polymer material having an anionic, cationic or amphoteric salt-forming group. WO 98/05283 published on Feb. 12, 1998 discloses a sheet like pack with defined shape and further comprising a keratotic plug-removal polymeric compound having a salt forming group.

WO 98/42302 published Oct. 1, 1998 discloses a flexible substrate sheet for removing keratotic plugs comprising an adhesive composition containing an anionic, cationic, non-ionic or amphoteric polymer such as polyvinyl pyrrolidone and poly(methyl vinyl ether/maleic anhydride) copolymer. WO 98/42304 published on Oct. 1, 1998 discloses a flexible non-occlusive substrate sheet for removing keratotic plugs containing an anionic or nonionic polymeric material such as the salts of poly(methyl vinyl ether/maleic anhydride) and polystyrene sulfonic acid and N-vinyl pyrrolidone.

Notwithstanding the above disclosures, there still is the need for additional skin cleaning and keratotic plug removing products, particularly one that is readily remoistenable and can be easily applied and effectively removed from the skin.

SUMMARY OF THE INVENTION

This invention relates to skin cleaning tapes for removing keratotic plugs and other debris and dirt found on the skin and in skin pores and comprising a poly(vinyl acetamide) polymer based adhesive composition applied to a substrate backing material. More particularly, this invention involves skin cleaning products comprising a polymer-based remoistenable adhesive composition wherein the polymer is a homopolymer of N-vinyl acetamide or an interpolymer prepared from N-vinyl acetamide and at least one other vinyl monomer.

This invention further involves a method for removing keratotic plugs from the skin using the selected remoistenable poly(vinyl acetamide) based adhesive as described herein.

DETAILED DESCRIPTION OF THE INVENTION

The present invention provides water-soluble, remoistenable, poly(vinyl acetamide) based adhesives for use as keratotic plug removers. The water soluble adhesives are coated or otherwise formed on a backing substrate which is then used to apply the adhesive composition to the skin to be treated.

The adhesive polymer used in this invention has good film forming properties, is easily remoistenable or re-wettable and provides good adhesion to the skin. More particularly, the adhesive polymer, poly(vinyl acetamide), i.e., PVAm is a homopolymer of N-vinyl acetamide (NVAm) or an interpolymer of NVAm and at least one other vinyl monomer. Preferably, the interpolymer will be prepared from at least about 10 percent by weight of NVAm, with the alance comprising vinyl monomer(s). Stated differently, the polymer will comprise from about 10 to 100 percent by weight of N-vinyl acetamide and from about 0 to 90 percent by weight of vinyl monomer. The preferred polymer is N-vinyl acetamide homopolymer.

The term "vinyl monomer", as used herein, refers to vinyl monomers which are copolymerizable with NVAm. Particularly suitable vinyl monomers include, (a) $C_1$–$C_{18}$ alkyl esters of acrylic acid; (b) $C_1$–$C_{18}$ alkyl esters of methacrylic acid; (c) vinyl esters of the formula $CH_2$=CH—OCOR where R is $C_1$–$C_{18}$; (d) alkyl substituted acrylamides and methacrylamides of the formula $CH_2$=CR—$CONR_1R_2$ where R is H or $CH_3$, $R_1$ is H or $C_1$–$C_{12}$ and $R_2$ is $C_1$–$C_{18}$; (e) hydroxy-substituted acrylates and methacrylates such as hydroxyethyl acrylate, hydroxypropyl acrylate, hydroxyethyl methacrylate, hydroxypropyl methacrylate and the like; (f) vinyl monomers containing an amine selected from the group consisting of secondary, tertiary and quaternary amines, such as n-vinyl imidazole, t-butylaminoethyl methacrylate (t-BAEM), dimethylaminoethyl methacrylate (DMAEMA), diethylaminoethyl methacrylate (DEAEMA), dimethylaminopropyl methacrylamide (DMAPMA) and the quarternized derivatives thereof such as methacrylatoethyltrimethyl ammonium chloride (MAPTAC), methacrylatoethyltrimethyl ammonium sulfate (MAETAS) and dimethyl diallyl ammonium chloride (DMDAAC); (g) acrylamide; and (h) non-alkyl substituted acrylamides such as diacetone acrylamide. Preferably, the vinyl comonomer is selected from the group consisting of methyl acrylate, methyl methacrylate, 2-hydroxyethyl acrylate, 2-hydroxyethyl methacrylate, 2-hydroxypropyl acrylate, 2-hydroxypropyl methacrylate, vinyl acetate, oligoethylene glycol monomethacrylate, and the vinyl monomers containing an amine selected from the group consisting of secondary, tertiary and quaternary amines.

The polymer, poly(vinyl acetamide), i.e., the homopolymer of N-vinyl acetamide or interpolymer of N-vinyl acetamide with vinyl monomer, as used in this invention, will generally have a weight average molecular weight of from about 30,000 to 2,000,000 and preferably from about 100,000 to 5,300,000.

Methods of making N-vinyl acetamide (NVAm) and the polymers thereof are known to those skilled in the art and are reported in Japanese publication numbers JP 08 81,428 published Mar. 26, 1996 and JP 08 134,029 published May 28, 1996. In the '428 publication N-(1-methoxyethyl) acetamide is prepared from dimethylacetal and acetamide in methanol and then thermally decomposed to obtain N-vinyl acetamide. Other methods are described in U.S. Pat. No. 4,942,259 issued Jul. 17, 1990 to G. Parris et al. where it is noted that percursors are formed and subsequently pyrolyzed or cracked to yield the desired vinyl amide. One such method is disclosed in U.S. Pat. No. 4,018,826 issued Apr. 19, 1977 to R. Gless et al. wherein acetaldehyde and acetamide are reacted to yield ethylidene-bis-acetamide which is thermally decomposed or cracked into vinyl acetamide. The '259 and '826 patents are hereby incorporated herein by reference.

A further embodiment of this invention is a blend of the poly(vinyl acetamide) polymer with one or more synthetic polymers or natural polymers. Examples of synthetic polymers which may be used include acrylate copolymers, acrylate/vinyl acetate copolymers, sodium polyacrylate, sodium polymethacrylate, polyvinylmethacrylate/methyl acrylate copolymers, octylacrylamide/acrylate/butylaminoethyl methacrylate copolymer, polyacrylamide, polyvinylacetate, vinylacetate/crotonic acid copolymer, vinyl acetate/crotonic acid/vinyl neodeconate copolymer, polyvinyl alcohol, polyvinyl formamide, and styrene/acrylate copolymers. Preferred synthetic polymers are polyvinyl formamide and copolymers thereof.

Natural polymers which may be blended with poly(vinyl acetamide) include starch, cellulose, guar gum and derivatives thereof. Useful derivatives of natural polymers include enzyme converted polymers, acid hydrolyzed polymers, oxidized polymers and polymers modified by etherification or esterification. Particularly useful modified polymers include hydroxyalkyl polymers prepared by etherification with alkylene oxides such as those containing 2 to 6, preferably 2 to 4 carbon atoms. Useful modified polymer esters include those with succinate, octenylsuccinate, acetate, propionate, butyrate, hexanoate and benzoate ester groups. Starch is a preferred natural polymer and particularly the hydroxyalkyl starches prepared by etherification with alkylene oxides as described above.

The proportion of poly(vinyl acetamide) to synthetic or natural polymers may vary from about 100:0 to 25:75 percent by weight.

The poly(vinyl acetamide) polymer or polymer blend may be used in an amount of from about 5 to 80% and preferably from about 15 to 65% by weight, based on the total weight of the liquid formulation. The polymers are dissolved in a solvent such as water, ethanol, isopropanol and mixtures thereof with water being the preferred solvent. The solvent generally comprises from about 20 to 95% by weight of the composition.

Additive components may optionally be added to the formulation of this invention, if desired, and such additives include U.V. absorbers, plasticizers, pigments, water swelling clay minerals, activators, vitamins and antiphogistics, fillers, surfactants, tack modifiers, skin modifiers, humectants and α- and β-hydroxy acids. Pigments which may be used include both organic and inorganic pigments such as titanium dioxide, silica and cellulose powders. A plasticizer can be added to the keratotic plug formulation and this can help in controlling the strength of the film when it is peeled from the skin and also improve the flexibility of a rigid polymer film. Examples of plasticizer components used in these compositions include; glycerin, propylene glycol, dipropylene glycol and butylene glycol. Typically, the additives will comprise from about 0.1 to 30% by weight of the formulation and preferably from about 0.5 to 10% by weight.

The skin cleaning tape of this invention is prepared by applying the water-soluble poly(vinyl acetamide) adhesive formulation to a suitable backing strip or substrate. The backing substrate may be a non-woven or woven strip or sheet such as cotton, rayon and nylon cloth, knits, nets or apertured films and any other conventional backing material such as used in adhesive tapes, packs and poultice.

The PVAm formulation is applied to the backing substrate on one side by conventional methods and one technique involves applying the formulation to the flexible backing or tape by coating it in the form of a solution in a suitable vehicle such as water or organic solvent and evaporating the vehicle to provide a dried remoistenable adhesive film. The tape or coated substrate is applied to the skin area to be cleaned, usually facial areas such as nose, forehead, chin or cheeks, which is first washed or wetted with water, normal soap or face wash. The tape or backing material is applied to the wet surface so that the adhesive film is re-wet and flows into the pores and attaches onto the keratotic plugs. The tape and film is allowed to dry, usually about 5 to 20 minutes, and then it, along with the dried adhesive film, is pulled off and removed from the skin. This mechanical action of removing the tape and adhesive causes the attached keratotic plugs as well as other attached dirt and debris to be pulled and removed from the pores.

Another technique of applying the PVAm formulation involves transfer coating in which the adhesive formulation is applied to a flexible release film. The coated film is then brought in contact with a backing substrate, the whole system dried and the solvent removed. The backing substrate is then removed leaving the dried film which is then applied to the skin area to be cleaned.

The following examples further illustrate the embodiments of this invention. In these examples, all parts and percentages are given by weight and all temperatures in degrees Celsius unless otherwise noted

EXAMPLE 1

A poly(vinyl acetamide) (PVAm) homopolymer with weight average molecular weight of about 250,000 was formulated into a composition which contained glycerin and titanium dioxide and had the following formulation:

| Ingredients | Parts by Weight |
| --- | --- |
| PVAm | 35 |
| Glycerin | 1 |
| Titanium Dioxide | 2 |
| Deionized Water | qs to 100 |

A nonwoven synthetic fiber was chosen as the backing for this system. In order to apply the composition to the backing, the formulation was coated onto a polyester film. The coating thickness on the polyester was 10 mil and this was controlled using a Bird Applicator. The nonwoven synthetic fiber was then laid on top of this coating and the whole system allowed to dry. Once the formulation was dried, the nonwoven was removed from the polyester and the coating had transferred from the polyester to the nonwoven. The film was white and very smooth and had no tack.

The dried film was then applied to the nose area of a human test model. The model first washed his face with soap and water and then applied this dried adhesive film to the wet tip of the nose. The adhesive film rewet and adhered to the skin. After drying for about 15 minutes, the pore cleansing strip was peeled from the nose. Keratotic plugs, dirt and other debris were quite visible on the pore cleansing tape after it was removed.

EXAMPLE 2

The same PVAm used in Example 1 was blended with a starch based polymer for use in this application. The converted starch based polymer composition was prepared using an α-amylase treated 35WF waxy corn starch modified with 9% propylene oxide and converted to 10 DE. The PVAm and the starch were blended and formulated into the following composition.

| Ingredients | Parts by Weight |
|---|---|
| α-amylase treated 35WF waxy corn with propylene oxide | 25 |
| Poly(vinyl acetamide) | 25 |
| Glycerin | 1 |
| Titanium Dioxide | 2 |
| Deionized Water | qs to 100 |

The formulation was applied to the nonwoven backing in Example 1. The film was white and very smooth and did not have tack. After application and removal, the tape again showed keratotic plugs, dirt, and other debris.

EXAMPLE 3

The same PVAm used in Example 1 was blended with another synthetic polymer, poly(vinyl formamide), and formulated into the following composition:

| Ingredients | Parts by Weight |
|---|---|
| Poly (vinyl acetamide) | 20 |
| Poly (vinyl formamide) | 20 |
| Glycerin | 1 |
| Titanium Dioxide | 2 |
| Deionized Water | qs to 100 |

The formulation was applied to the nonwoven backing as in Example 1. The dried film was white and had no tack. After application and removal, the tape again showed keratotic plugs, dirt, and other debris.

What is claimed is:

1. A skin cleaning product comprising a substrate backing material with a poly(vinyl acetamide) polymer based adhesive composition applied to one surface of the substrate, the poly(vinyl acetamide) being a homopolymer of N-vinyl acetamide or an copolymer of N-vinyl acetamide and at least one other vinyl monomer.

2. The skin care product of claim 1 wherein the adhesive composition is a liquid formulation comprising from about 5 to 80% by weight of poly(vinyl acetamide) polymer.

3. The skin care product of claim 1 wherein the vinyl monomer is selected from the group consisting of (a) $C_1$–$C_{18}$ alkyl esters of acrylic acid; (b) $C_1$–$C_{18}$ alkyl esters of methacrylic acid; (c) vinyl esters of the formula $CH_2$=CH—OCOR where R is $C_1$–$C_{18}$; (d) alkyl substituted acrylamides and methacrylamides of the formula $CH_2$=CR—$CONR_1R_2$ where R is H or $CH_3$, $R_1$ is H or $C_1$–$C_{12}$ and $R_2$ is $C_1$–$C_{18}$; (e) hydroxy functional acrylates and methacrylates; (f) vinyl monomers containing an amine selected from the group consisting of secondary, tertiary and quaternary amines; (g) acrylamide; and (h) non-alkyl substituted acrylamide.

4. The skin care product of claim 1 wherein the polymer is prepared from 10 to 100 weight percent of N-vinyl acetamide and from about 0 to 90 weight percent of the vinyl monomer.

5. The skin care product of claim 1 wherein the polymer is the homopolymer of N-vinyl acetamide.

6. The skin care product of claim 1 wherein the adhesive composition comprises a blend of the poly(vinyl acetamide) and a synthetic or natural polymer in amounts of from 100:0 to 25:75 percent by weight of poly(vinyl acetamide) to synthetic or natural polymer.

7. The skin care product of claim 6 wherein the adhesive composition comprises a blend of poly(vinyl acetamide) and a natural polymer selected from the group consisting of starch, cellulose, guar gum and derivatives thereof.

8. The skin care product of claim 7 wherein the poly(vinyl acetamide) is the homopolymer of N-vinyl acetamide.

9. The skin care product of claim 5 wherein the synthetic polymer is polyvinyl formamide and copolymers thereof.

10. The skin care product of claim 2 wherein the polymer is prepared from 10 to 100 weight percent of N-vinyl acetamide and from about 0 to 90 weight percent of the vinyl monomer.

11. The skin care product of claim 10 wherein the adhesive composition comprises a blend of the poly(vinyl acetamide) and a synthetic or natural polymer in amounts of from 100:0 to 25:75 percent by weight of poly(vinyl acetamide) to synthetic or natural polymer.

12. The skin care product of claim 4 wherein the adhesive composition is a liquid formulation comprising from about 15 to 65% by weight of poly(vinyl acetamide) polymer.

13. The skin care product of claim 12 wherein the adhesive composition comprises a blend of the poly(vinyl acetamide) and a synthetic or natural polymer in amounts of from 100:0 to 25:75 percent by weight of poly(vinyl acetamide) to synthetic or natural polymer.

14. The skin care product of claim 10 wherein the vinyl monomer is selected from the group consisting of (a) $C_1$–$C_{18}$ alkyl esters of acrylic acid; (b) $C_1$–$C_{18}$ alkyl esters of methacrylic acid; (c) vinyl esters of the formula $CH_2$=CH—OCOR where R is $C_1$–$C_{18}$; (d) alkyl substituted acrylamides and methacrylamides of the formula $CH_2$=CR—$CONR_1R_2$ where R is H or $CH_3$, $R_1$ is H or $C_1$–$C_{12}$ and $R_2$ is $C_1$–$C_{18}$; (e) hydroxy functional acrylates and methacrylates; (f) vinyl monomers containing an amine selected from the group consisting of secondary, tertiary and quaternary amines; (g) acrylamide; and (h) non-alkyl substituted acrylamide.

15. The method of removing keratotic plugs and other dirt from skin surfaces which comprises applying a poly(vinyl acetamide) based adhesive composition which is attached to a substrate backing material to a wet skin surface, allowing the wetted adhesive composition to dry and removing the dried composition and backing material from the skin along with attached keratotic plugs and other dirt, wherein the poly(vinyl acetamide) is a homopolymer of N-vinyl acetamide or an copolymer of N-vinyl acetamide and at least one other vinyl monomer.

16. The method of claim 15 wherein the adhesive composition is a liquid formulation comprising from about 5 to 80% by weight of poly(vinyl acetamide) polymer.

17. The method of claim 16 wherein the polymer is prepared from 10 to 100 weight percent of N-vinyl acetamide and from about 0 to 90 weight percent of the vinyl monomer.

18. The method of claim 17 wherein the adhesive composition comprises a blend of the poly(vinyl acetamide) and a synthetic or natural polymer in an amount of from 100:0 to 25:75 percent by weight of poly(vinyl acetamide) to synthetic or natural polymer.

19. The method of claim 16 wherein the poly(vinyl acetamide) is the homopolymer of N-vinyl acetamide.

20. The method of claim 19 wherein the adhesive composition comprises a blend of the N-vinyl acetamide homopolymer and a natural polymer selected from the group consisting of starch, cellulose, guar gum and derivatives thereof.

* * * * *